(12) United States Patent
Taber et al.

(10) Patent No.: US 10,561,447 B2
(45) Date of Patent: Feb. 18, 2020

(54) INTERSPINOUS IMPLANTS WITH DEPLOYABLE WING

(71) Applicant: Zimmer Biomet Spine, Inc., Broomfield, CO (US)

(72) Inventors: Justin Taber, Lafayette, CO (US); Patrick Hunt, Denver, CO (US); Andrew Lamborne, Golden, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 174 days.

(21) Appl. No.: 15/672,786

(22) Filed: Aug. 9, 2017

(65) Prior Publication Data
US 2017/0333090 A1    Nov. 23, 2017

Related U.S. Application Data

(63) Continuation of application No. 14/652,475, filed as application No. PCT/US2013/078483 on Dec. 31, 2013, now Pat. No. 9,750,544.

(60) Provisional application No. 61/747,726, filed on Dec. 31, 2012.

(51) Int. Cl.
*A61B 17/70*    (2006.01)

(52) U.S. Cl.
CPC ...... *A61B 17/7068* (2013.01); *A61B 17/7061* (2013.01); *A61B 17/7065* (2013.01)

(58) Field of Classification Search
CPC ............ A61B 17/7065; A61B 17/7068; A61B 17/7062; A61B 2017/0256
See application file for complete search history.

(56) References Cited

U.S. PATENT DOCUMENTS

| | | | |
|---|---|---|---|
| 2,077,804 A | 4/1937 | Monroe | |
| 4,721,103 A | 1/1988 | Freedland | |
| 5,098,433 A | 3/1992 | Freedland | |
| 8,075,593 B2 | 12/2011 | Hess | |
| 8,097,019 B2 | 1/2012 | Mitchell et al. | |

(Continued)

FOREIGN PATENT DOCUMENTS

WO    WO-2014106246 A1    7/2014

OTHER PUBLICATIONS

"U.S. Appl. No. 14/652,475, Non Final Office Action dated Sep. 28, 2016", 19 pgs.

(Continued)

*Primary Examiner* — Jacqueline T Johanas
(74) *Attorney, Agent, or Firm* — Schwegman Lundberg & Woessner, P.A.

(57) ABSTRACT

The present invention provides spinous process implants and associated methods. In one aspect of the invention, the implant includes at least one extension with a superior lobe pivotally connected to an inferior lobe, such as by a hinge, to allow unfolding of the at least one extension from a folded position to an unfolded position. In certain aspects, the folding extension may include fasteners to facilitate engagement with the spinous processes to provide both a flexion stop as well as an extension stop. The fasteners may have corresponding bores to allow the fasteners to reside in the bores to provide a compact profile for implantation. In another aspect of the invention, the implant is introduced to the surgical site using a lateral or paramedian approach and associated tools to facilitate the same.

15 Claims, 14 Drawing Sheets

(56) References Cited

U.S. PATENT DOCUMENTS

| | | | |
|---|---|---|---|
| 8,172,878 B2 | 5/2012 | Yue | |
| 8,403,959 B2 | 3/2013 | Döllinger | |
| 8,747,440 B2 | 6/2014 | Yue | |
| 8,945,184 B2 | 2/2015 | Hess et al. | |
| 9,039,742 B2 | 5/2015 | Altarac et al. | |
| 9,314,276 B2 | 4/2016 | Hess et al. | |
| 9,750,544 B2 | 9/2017 | Taber et al. | |
| 2005/0245937 A1 | 11/2005 | Winslow | |
| 2006/0064166 A1* | 3/2006 | Zucherman | A61B 17/7065 623/17.11 |
| 2006/0271194 A1* | 11/2006 | Zucherman | A61B 17/7065 623/17.11 |
| 2007/0173832 A1 | 7/2007 | Tebbe et al. | |
| 2007/0270840 A1 | 11/2007 | Chin et al. | |
| 2008/0071280 A1 | 3/2008 | Winslow | |
| 2008/0108990 A1 | 5/2008 | Mitchell et al. | |
| 2008/0177391 A1 | 7/2008 | Mitchell et al. | |
| 2008/0183211 A1 | 7/2008 | Lamborne et al. | |
| 2008/0221692 A1* | 9/2008 | Zucherman | A61B 17/7053 623/17.16 |
| 2008/0287997 A1* | 11/2008 | Altarac | A61B 17/7065 606/249 |
| 2009/0054988 A1 | 2/2009 | Hess | |
| 2009/0138046 A1* | 5/2009 | Altarac | A61B 17/7065 606/249 |
| 2009/0254185 A1 | 10/2009 | Döllinger | |
| 2010/0057130 A1 | 3/2010 | Yue | |
| 2010/0106191 A1 | 4/2010 | Yue et al. | |
| 2010/0152775 A1* | 6/2010 | Seifert | A61B 17/3468 606/249 |
| 2010/0234889 A1 | 9/2010 | Hess | |
| 2011/0066186 A1 | 3/2011 | Boyer, II et al. | |
| 2011/0172711 A1* | 7/2011 | Kirschman | A61B 17/7068 606/252 |
| 2011/0190816 A1* | 8/2011 | Sheffer | A61B 17/7062 606/249 |
| 2012/0078301 A1 | 3/2012 | Hess | |
| 2012/0089185 A1* | 4/2012 | Gabelberger | A61F 2/4405 606/249 |
| 2012/0109205 A1 | 5/2012 | Mitchell et al. | |
| 2012/0265246 A1 | 10/2012 | Yue | |
| 2012/0265251 A1 | 10/2012 | Yue | |
| 2015/0305785 A1 | 10/2015 | Taber et al. | |

OTHER PUBLICATIONS

"U.S. Appl. No. 14/652,475, Notice of Allowance dated May 9, 2017", 9 pgs.

"U.S. Appl. No. 14/652,475, Response filed Sep. 15, 2016 to Restriction Requirement dated Aug. 3, 2016", 8 pgs.

"U.S. Appl. No. 14/652,475, Response filed Dec. 28, 2016 to Non Final Office Action dated Sep. 28, 2016", 19 pgs.

"U.S. Appl. No. 14/652,475, Restriction Requirement dated Aug. 3, 2016", 8 pgs.

"International Application Serial No. PCT/US2013/078483, International Preliminary Report on Patentability dated Jul. 9, 2015", 12 pgs.

"International Application Serial No. PCT/US2013/078483, International Search Report dated Apr. 28, 2014", 7 pgs.

"International Application Serial No. PCT/US2013/078483, Written Opinion dated Apr. 28, 2014", 10 pgs.

* cited by examiner

INTERSPINOUS IMPLANTS WITH DEPLOYABLE WING

CROSS-REFERENCE TO RELATED APPLICATIONS

This application is related to U.S. patent application Ser. No. 11/934,604, filed Nov. 2, 2007, now U.S. Pat. No. 8,241,330, titled Spinous Process Implants and Associated Methods; U.S. patent application Ser. No. 12/020,282, filed Jan. 25, 2008, titled Spinal Implants and Methods; U.S. patent application Ser. No. 12/751,856, filed Mar. 31, 2010, titled Spinous Process Implants and Associated Methods; U.S. patent application Ser. No. 12/538,710, filed Aug. 10, 2009, now U.S. Pat. No. 8,382,801, titled Spinous Process Implants, Instruments, and Methods; and U.S. patent application Ser. No. 12/854,125, filed Aug. 10, 2010, titled Interspinous Implants and Methods, all of which are incorporated herein by reference as if set out in full.

FIELD

The present disclosure relates to interspinous implants that facilitate distraction and fusion of a spine and, more particularly, to an interspinous implant that may be easier to implant percutaneously.

BACKGROUND

The vertebrae of the human spine are arranged in a column with one vertebra on top of the next. An intervertebral disc lies between adjacent vertebrae to transmit force between the adjacent vertebrae and provide a cushion between them. The discs allow the spine to flex and twist. With age or injury, spinal discs begin to break down, or degenerate, resulting in the loss of fluid in the discs, and consequently, the discs become less flexible. Likewise, the discs become thinner allowing the vertebrae to move closer together. Degeneration also may result in tears or cracks in the outer layer, or annulus, of the disc. The disc may begin to bulge outwardly. In more severe cases, the inner material of the disc, or nucleus, may actually extrude out of the disc. In addition to degenerative changes in the disc, the spine may undergo changes due to trauma from automobile accidents, falls, heavy lifting, and other activities. Furthermore, in a process known as spinal stenosis, the spinal canal narrows due to excessive bone growth, thickening of tissue in the canal (such as ligament), or both. In all of these conditions, the spaces through which the spinal cord and the spinal nerve roots pass may become narrowed leading to pressure on the nerve tissue which can cause pain, numbness, weakness, or even paralysis in various parts of the body. Finally, the facet joints between adjacent vertebrae may degenerate and cause localized and/or radiating pain. All of the above conditions, as well as others not specifically mentioned, are collectively referred to herein as spine disease.

Conventionally, surgeons treat spine disease by attempting to restore the normal spacing between adjacent vertebrae. This may be sufficient to relieve pressure from affected nerve tissue. However, it is often necessary to surgically remove disc material, bone, or other tissues that impinge on the nerve tissue and/or to debride the facet joints. Most often, the restoration of vertebral spacing is accomplished by inserting a rigid spacer made of bone, metal, or plastic into the disc space between the adjacent vertebrae and allowing the vertebrae to grow together, or fuse, into a single piece of bone. The vertebrae are typically stabilized during this fusion process with the use of bone plates and/or pedicle screws fastened to the adjacent vertebrae.

Although techniques for placing intervertebral spacers, plates, and pedicle screw fixation systems have become less invasive in recent years, they still require the placement of hardware deep within the surgical site adjacent to the spine. Recovery from such surgery can require several days of hospitalization and long, slow rehabilitation to normal activity levels.

Rather than spinal fusion, investigators have promoted the use of motion preservation implants and techniques in which adjacent vertebrae are permitted to move relative to one another. One such implant that has met with only limited success is the artificial disc implant. The artificial disc typically includes either a flexible material or a two-piece articulating joint inserted in the disc space. Another such implant is the spinous process spacer which is inserted between the posteriorly extending spinous processes of adjacent vertebrae to act as an extension stop and to maintain a minimum spacing between the spinous processes when the spine is in extension. The spinous process spacer allows the adjacent spinous processes to move apart as the spine is flexed. The extension stop spacers, however, also have had limited success.

Recently, the trend has been back towards fusion devices rather than motion preservation devices. One promising recent implant is a spinal process fusion plate. Similar to the fusion implants, the spinal process fusion plate promotes fusion between adjacent vertebrae to relieve pressure on the nerve. However, unlike more conventional spinal implant systems, the spinal process fusion plate facilitates less invasive procedures than conventional spinal fusion surgery. The need still exists for improved spinal process fusion plates to facilitate even less invasive surgery including, minimally invasive surgery, percutaneous implantation, and the like.

BRIEF DESCRIPTION OF THE DRAWINGS

Various examples of the technology of the present application will be discussed with reference to the appended drawings. These drawings depict only illustrative examples of the technology described more fully herein and are not to be considered limiting of its scope.

DESCRIPTION OF THE ILLUSTRATIVE EXAMPLES

Figure 1:
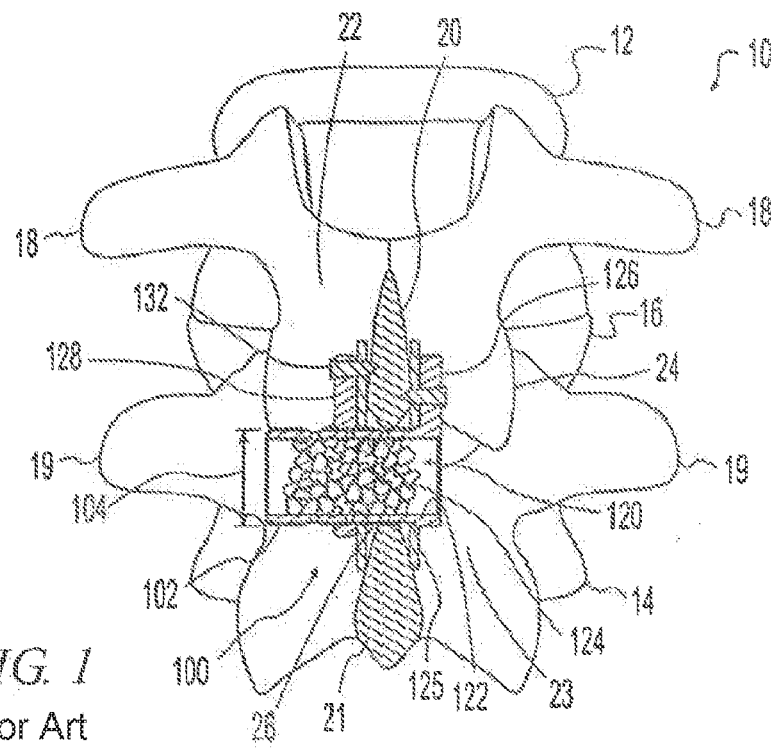
FIG. 1 is a posterior cross sectional view of an implant in situ that is deployed using a tool consistent with the technology of the present application.

The technology of the present application will be described in the context of spinal surgery, but one of ordinary skill in the art will recognize on reading the disclosure that the technology may be applicable to other medical fields. Moreover, the technology of the present application will be described with reference to certain exemplary embodiments. The word "exemplary" is used herein to mean "serving as an example, instance, or illustration." Any embodiment described herein whether or not specifically identified as "exemplary" is not to be construed as preferred or advantageous over other embodiments. Further, the instrument(s) described in accordance with the technology of the present application facilitate surgical implantation of spinal process fusion plates. With that in mind, exemplary spinous process implants, according to the technology, may include a spacer and an extension extending outwardly from the spacer. The extension, which may be referred to as a wing, is sometimes described as being one or more lobes associated with the spacer. The spinous process implant may be configured for insertion between adjacent spinous processes of the cervical, thoracic, and/or lumbar spine. The spacer may be provided in a variety of sizes to accommodate anatomical variation amongst patients and varying degrees of space correction. The spacer and extensions may include openings to facilitate tissue in-growth to anchor the spacer to the vertebral bodies such as tissue in-growth from the spinous processes. The spacer may be configured for tissue in-growth from superior and inferior spinous processes to cause fusion of the adjacent spinous processes. The openings may be relatively large and/or communicate to a hollow interior of the spacer. A hollow interior may be configured to receive bone growth promoting substances such as by packing the substances into the hollow interior. The openings may be relatively small and/or comprise pores or interconnecting pores over at least a portion of the spacer surface. The openings may be filled with bone growth promoting substances.

The extension may extend transversely from the spacer relative to a spacer longitudinal axis to maintain the spacer between adjacent spinous processes. The extension may be described as foldable, extendable, deployable or the like from a flat configuration to facilitate minimally invasive implantation to an extended position to facilitate fusion. A single extension may extend in one or more directions or multiple extensions may be provided that extend in multiple directions. One or more extensions may be adjustable longitudinally relative to one another and/or the spacer to allow the extensions to be positioned laterally relative to the spinous processes. A moveable extension may be provided that is moveable axially relative to the spacer and another extension. Alternatively, a plurality of moveable extensions may be provided. For example, the extensions may clamp against the sides of the spinous processes to immobilize the spinous processes relative to one another and promote fusion between the adjacent vertebrae. The extensions may include fasteners engageable with the spinous processes. The fasteners may include sutures, wires, pins, straps, clamps, spikes, screws, teeth, adhesives, and/or other suitable fasteners. The fasteners may be integrated into the extensions or they may be modular. Modular fasteners may be adjustable, replaceable, and/or removable to allow tailoring of the kind and quality of fixation from rigid fixation to no fixation. The spacer, extensions, and/or fasteners may advantageously be made of different materials. For example, the spacer and extensions may be made of a relatively softer material while the fasteners may be made of a relatively harder material. For example, the spacer and/or extension may be made of a polymer and/or other relatively soft material and the fastener may be made of a metal and/or other relatively hard material.

Insertion of spinous process implants may be facilitated by a set of instruments alternately engageable with one another to increase the interspinous space and engageable with a spinous process implant to help maneuver it between adjacent spinous processes as has been described in some of the related applications described above and incorporated by reference. Moreover, instruments for the present spinous process implant may facilitate percutaneous operation whether through a cannula, tube, or lumen. The instruments may include mechanisms to facilitate unfolding, opening, or deploying foldable extensions. The instruments may include a draw internal or external to the spacer to pull the extensions in a direction such that the extensions are pried apart by a wedge or ramp.

It has been found that presently available interspinous implants, such as the device explained with reference to FIGS. 1-9, are good at stabilizing a spinal segment to allow it to fuse. The interspinous implant could be implanted with less tissue trauma, however, if one or more of the extensions could fold or pivot to allow insertion percutaneously or through a tube, cannula or lumen. In certain embodiments, one or more of the extensions may have offset fasteners on the foldable extension and corresponding bore into which the fasteners may fit to allow a flat or nearly flat configuration of the folded wing for the most compact delivery possible. The foldable extensions may fold about an axle or be hinged to allow for movement. A draw, rod, or hook may be connected to the hinge or axle to pull the hinge or axle towards the spacer that causes the face or surface of the extension to run up against an edge that forces the folded extension to unfold. In some embodiments, internal rods and ramps may be used to force the folded extension to unfold or open.

Reference will now be made to FIGS. 1-9 describing an exemplary embodiment of a spinous process implant with fixed or non-foldable extensions. One or both of the fixed, non-foldable extensions could be replaced with the foldable extensions described further herein, but the description of the spinous process implant with fixed, non-foldable extensions is provided for completeness. While a specific exemplary embodiment is provided herein, implants associated with any of the incorporated applications or similar spinous process fusion plates may benefit from the technology of the present application to allow fixed extensions or wings to fold to facilitate implantation.

Figure 2:
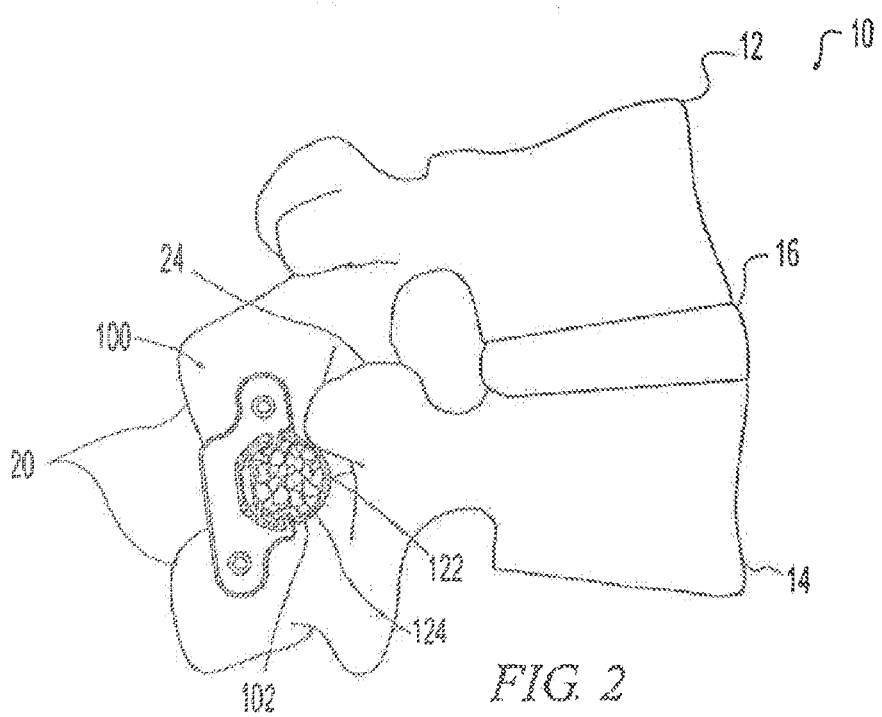
FIG. 2 is a side elevational view of the implant of FIG. 1 in situ.

FIGS. 1 and 2 depict posterior and lateral views of a pair of adjacent vertebrae of the lumbar spine 10. A superior vertebra 12 is separated from an inferior vertebra 14 by a disc 16. Each vertebra includes a pair of transverse processes 18, 19, a posteriorly projecting spinous process 20, 21, and a pair of lamina 22, 23 connecting the transverse processes 18, 19 to the spinous process 20, 21. In addition to the connection through the disc 16, the vertebrae 12, 14 articulate at a pair of facet joints 24.

FIGS. 1-9 illustrate an exemplary spinous process implant 100. The implant 100 includes a spacer 102 positioned between the spinous processes 20, 21. The geometry of the implant 100 is illustrated with the use of axes that define length (l), height (h), and width (w) directions for the spacer. When implant 100 is implanted in a patient, the height direction of the spacer 102 is generally oriented along the superior/inferior direction of the patient's anatomy, the width direction of the spacer 102 is generally oriented along the anterior/posterior direction of the patient's anatomy, and the length direction of the spacer 102 is generally oriented along the lateral/medial direction of the patient's anatomy.

The height 104 (FIG. 1) of spacer 102 limits how closely the spinous processes 20, 21 can move together. As the implant in this example is a fusion plate, the height also limits how distantly the spinous processes 20, 21 can move apart. Thus, the spacer 102 maintains a minimum and maximum distance between the spinous processes 20, 21. In the case of spine disease involving posterior subsidence of the adjacent vertebra, insertion of the spacer 102 between the spinous processes 20, 21 will move the vertebrae apart and relieve pressure on nerve tissue and the facet joints 24.

Figure 3:
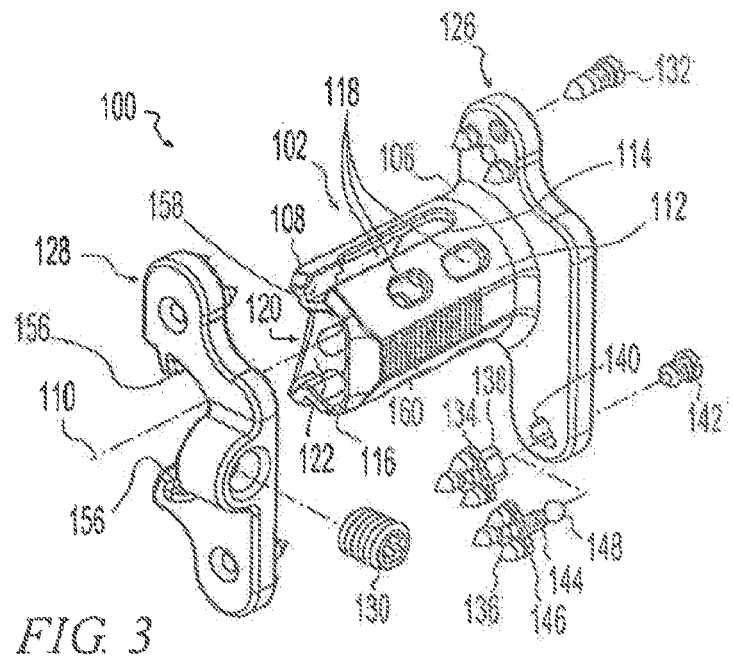
FIG. 3 is an exploded perspective view of the implant of FIG. 1.

As shown in FIG. 3, the spacer 102 includes a first end 106, a second end 108, and a longitudinal axis 110 extending from the first end to the second end. The spacer 102 has a sidewall 112, generally parallel to the longitudinal axis 110, including superior and inferior outer surfaces 114, 116. Transverse openings 118 (see also FIG. 6) communicate from the superior and inferior outer surfaces 114, 116 inwardly to facilitate tissue in-growth. The exemplary spacer 102 includes a hollow interior 120 bounded by an inner surface 122 such that the openings 118 communicate from the outer surfaces 114, 116 to the hollow interior 120. Bone growth promoting substances 124 are shown packed into the hollow interior 120 in FIGS. 1 and 2 to promote fusion of the vertebrae 12, 14 by bone growth between the spinous processes 20, 21.

The spinous process implant 100 further includes a first extension 126 projecting outwardly from the spacer 102 along the spacer height direction h and transversely to the longitudinal axis 110 to lie generally alongside the superior and inferior spinous processes 20, 21. Abutment of the first extension 126 with the spinous processes 20, 21 helps prevent lateral movement of spacer 102, thereby maintaining spacer 102 between the spinous processes 20, 21. In the exemplary spinous process implant 100, the first extension 126 is fixed relative to the spacer 102 and the implant includes a second extension 128 mountable to the spacer for axial movement relative to the first extension 126. The second extension 128 may be moved toward the first extension 126 to approximate the width of the spinous processes 20, 21 and better stabilize the implant 100. It is fixed in place by tightening a set screw 130 (FIG. 3) against the spacer 102. The extensions 126, 128 include fasteners 132, 134, 136 projecting from the extensions 126, 128 to engage the spinous processes 20, 21 to fix the spacer 102 to the spinous processes 20, 21. FIG. 1 depicts an additional bone growth promoting substance in the form of strips of bone 125 sandwiched between the extensions 126, 128 along the sides of the spinous processes 20, 21 to promote bone growth along the sides of the spinous processes to further enhance fusion of the vertebrae 12, 14. The extensions 126, 128 preferably extend inferiorly as well as superiorly from spacer 102 to optionally attach to the inferior spinous processes to immobilize the spinous processes 20, 21 relative to one another while fusion takes place.

Fasteners 132, 134, and 136 may take any suitable form. They may be made integral with the extensions 126, 128 such as by machining or casting them with the extensions or they may be formed separately and permanently attached to the extensions 126, 128. Fastener 132 is a sharpened spike that threadably engages the extension 126. The threaded engagement allows the fastener 132 to be replaced with a different fastener 132. For example, the fastener 132 may be replaced by one that has a different shape, a different size, a different material, or a different surface coating. The threaded engagement also allows the fastener 132 to be adjusted to extend by varying amounts from the extension 126 to vary how it engages the bone. Thus, the fastener 132 can be adjusted to fit differently shaped bones or to penetrate into a bone by varying amounts. For example, multiple threaded fasteners 132 can be adjusted to extend by different amounts to conform to curved or angled bone. Finally, the threaded engagement allows the user to remove the fastener 132 when fixation is not desired such as when it is desired to use implant 100 in a non-fusion procedure as an extension stop without limiting flexion.

As best seen in FIG. 3, fasteners 134 and 136 are provided as multi-spike pods allowing a plurality of spikes to be quickly adjusted, changed, or omitted. Fastener 134 includes a non-circular tab 138 engageable with a non-circular opening 140 in the extension 126. The non-circular engagement prevents the fastener 134 from rotating. The tab 138 may form a press-fit, snap-fit, or other suitable engagement with the opening 140. The tab 138 may be further secured by a supplemental screw 142. Fastener 136 includes a threaded shaft 144 threadably engaged with a base member 146 to allow the length of the fastener 136 to be adjusted. The shaft 144 engages the extension 126 in a rotating and pivoting manner such that the fastener 136 can be adjusted rotationally and angularly to engage the bone surface. In the illustrative embodiment, the shaft 144 terminates in a spherical ball 148 that engages the opening 140 in a ball-and-socket arrangement for three degrees of freedom. However, any mechanism that allows any number of degrees of freedom may be used. The fastener 136 may be allowed to move in use so that as the extension 126 is pressed toward a bone, the fastener 136 adjusts to the angle of the bone surface. The fastener 136 also may be secured, such as by screw 142, to adjust the tension in the joint and/or to lock the fastener 136 in a predetermined orientation.

Figure 4:
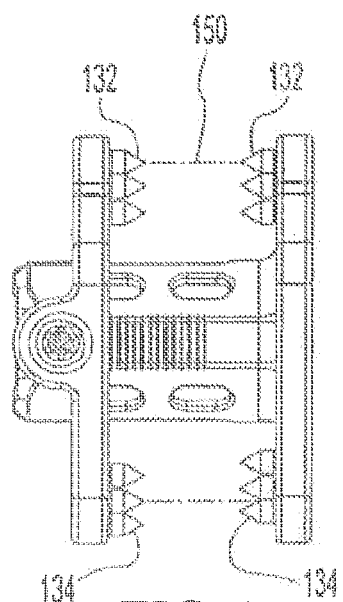
FIG. 4 is a posterior elevational view of the implant of FIG. 1.

FIG. 4 illustrates the axial relationship of fasteners on the opposing extensions 126, 128. In the illustrative implant 100, the fasteners 132 at the top of the implant 100 are shown aligned along a common axis 150 that is substantially perpendicular to extensions 126 and 128. The fasteners 134 at the bottom of the implant 100 are shown offset so that they can interleave, if necessary, as they are pressed into a bone. Any combination of fastener type, number, and alignment may be provided on the implant 100.

Figure 5:
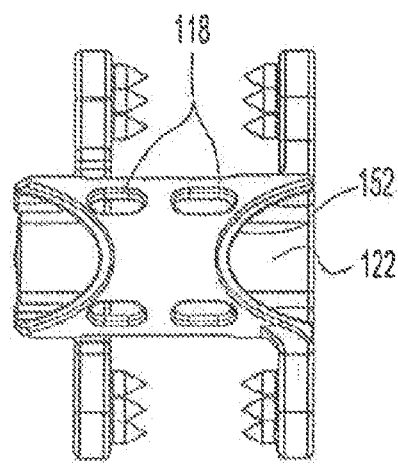
FIG. 5 is an anterior elevational view of the implant of FIG. 1.
Figure 6:
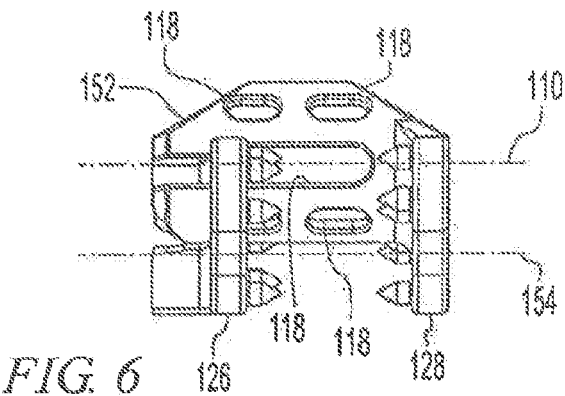
FIG. 6 is a top plan view of the implant of FIG. 1.

As seen in FIGS. 5 and 6, the ends 106, 108 of the spacer 102 include anterior chamfers 152. These chamfers 152 allow the ends 106, 108 to clear posteriorly facing structures of the vertebrae 12, 14 such as the facet joints 24. Also, as seen in FIGS. 5 and 6, the spacer 102 is offset anteriorly (in the spacer width direction w) relative to the extensions 126, 128 such that the longitudinal axis 110 of the spacer 102 is anterior of a midline plane 154 (FIGS. 6, 8) of the extensions 126, 128. The anterior offset of the spacer 102 allows it to fit deeply between the spinous processes 20, 21 while the extensions 126, 128 fit alongside the spinous processes 20, 21.

Figure 7:
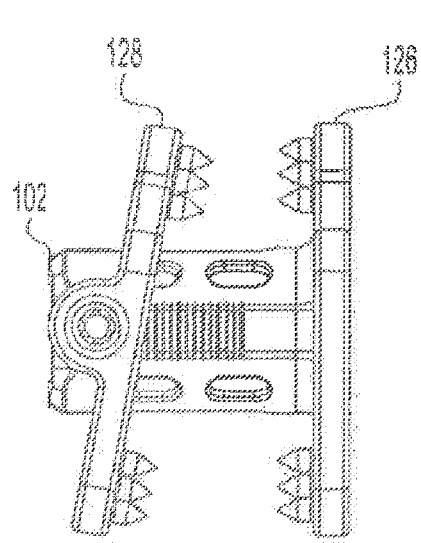
FIG. 7 is a posterior elevational view of the implant of FIG. 1 showing the assembly in an alternate position.
Figure 8:
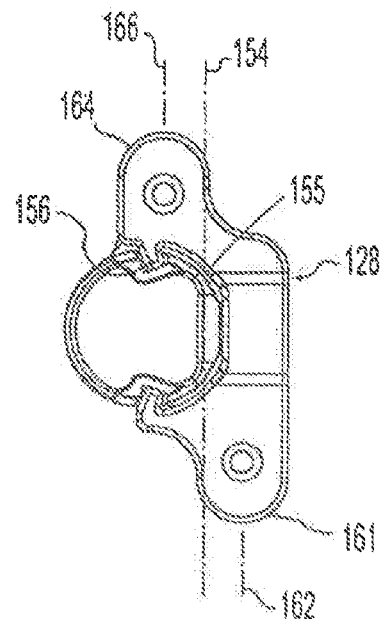
FIG. 8 is a side elevational view of the implant of FIG. 1.

As best seen in FIGS. 3 and 8, the second extension 128 defines an aperture 155 conforming generally to the cross-sectional shape of the spacer 102. In the illustrative embodiment of FIGS. 1-9, the aperture 155 opens anteriorly to form a "C"-shape. Tabs 156 extend inwardly from the superior and inferior portions of the aperture to slidingly engage elongated slots 158 in the superior and inferior surfaces of the spacer 102. The second extension 128 can be translated longitudinally along the spacer length l toward and away from the first extension 126. Tightening the set screw 130 against the posterior side 160 of the spacer 102 forces the tabs 156 posteriorly against the sides of the slots 158 and locks the second extension 128 in place longitudinally. The posterior side 160 of the spacer 102 may be roughened as shown to better grip the set screw 130. The set screw 130 may also dig into the surface of the spacer 102 upon tightening to positively grip the spacer 102. The aperture 155 (FIGS. 3, 8) may conform closely to the spacer 102 to constrain the second extension 128 to generally parallel motion relative to the first extension 126. Alternatively, the aperture 155 may be larger than the spacer 102 by a predetermined amount to permit a predetermined amount of angular adjustment of the second extension 128 relative to the first extension 126 as shown in FIG. 7 to allow the extension 128 to adjust to the underlying bone surface.

Figure 9:
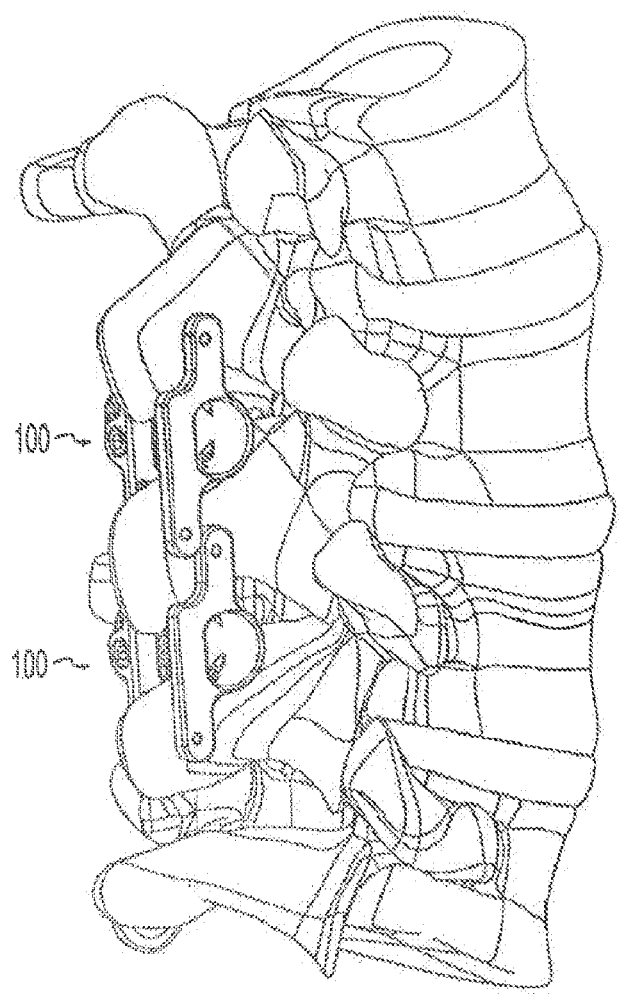
FIG. 9 is a perspective view of a pair of implants like that of FIG. 1 in situ.

As best seen in FIG. 8, the second extension 128 includes a first inferior lobe 161 having a first lobe centerline 162 and a second superior lobe 164 having a second lobe centerline 166. In the illustrative embodiment, the first lobe centerline 162 and the second lobe centerline 166 are parallel and spaced apart so that the second extension 128 has a generally "Z"-shaped plan form. This shape allows the extension of one implant 100 to interleave, if necessary, with another implant 100 in a multilevel surgery (as shown in FIG. 9) to permit close spacing of the implants, and/or longer extension lobes for more extensive bone engagement. In addition, first inferior lobe 161 has a semi-circular convex shape that is generally complementary to a semi-circular superior concave surface 165 formed adjacent second superior lobe 164. Similarly, second superior lobe 164 has a semi-circular convex shape that is generally complementary in shape to a semi-circular inferior concave surface 163 formed adjacent first inferior lobe 161. As indicated in FIG. 8, first inferior lobe 161 is adjacent to inferior concave surface 163, and extension midline plane 154 is located between first inferior lobe 161 and inferior concave surface 163. Second superior lobe 164 is adjacent superior concave surface 165, and extension midline plane 154 is located between second superior lobe 164 and superior concave surface 165. Moreover, first inferior lobe radius $r_1$ is substantially equal to superior concave surface radius $r_4$, while second superior lobe radius $r_3$ is substantially equal to inferior concave surface radius $r_2$. As a result, when two implants are placed on adjacent spinal levels, the first inferior lobe 161 of the upper implant may be (but need not be, depending on what is medically indicated) interfitted into the superior concave surface 165 of the inferior implant. In addition, the second superior lobe 164 of the inferior implant may be interfitted into the inferior concave surface 163 of the superior implant. In the illustrative example of FIGS. 1-9, first inferior lobe 161 and second superior lobe 164 form a unitary second extension 128. Although not separately depicted, first extension 126 also has complementary lobes that are similarly configured and oriented relative to one another.

As shown in FIG. 9, multiple spinous process implants 100 may be placed on adjacent levels of the spine. As illustrated in the figure, a first superior implant 100 is positioned with its spacer 102 between a first superior spinous process and a second intermediate spinous process, while a second inferior implant 100 is positioned with its spacer 102 between the second intermediate spinous process and a third inferior spinous process. The first extensions 126 of the superior and inferior implants are located on a first side of the patient's sagittal plane, while the second extensions 128 of the superior and inferior implants are located on a second side of the patient's sagittal plane.

In the illustrative embodiment of FIGS. 1-9, the extension lobe centerlines 162, 166 are offset equidistantly from the midline plane 154 of the second extension 128. Although not separately shown, the first extension 126 is configured similarly. The centerlines 162, 166 may vary from parallel and they may be offset asymmetrically to form different shapes to accommodate different vertebral anatomy. For example, the shape may be tailored for different portions of the spine 10. In the illustrative embodiment of FIGS. 1-9, the first extension 126 has the same shape as the second extension 128. However, the shape may be varied between the first and second extensions 126, 128.

As shown in FIGS. 1-9, the first extension 126 is integral or unitary with the spacer 102 and second extension 128 has an aperture 155 that is shown to partially surround the spacer to allow the second extension 128 to translate over the outer surface of the spacer 102. In certain embodiments, especially smaller implants, the aperture 155 may form a through hole in second extension 128 to completely surround the spacer 102.

Figure 10:
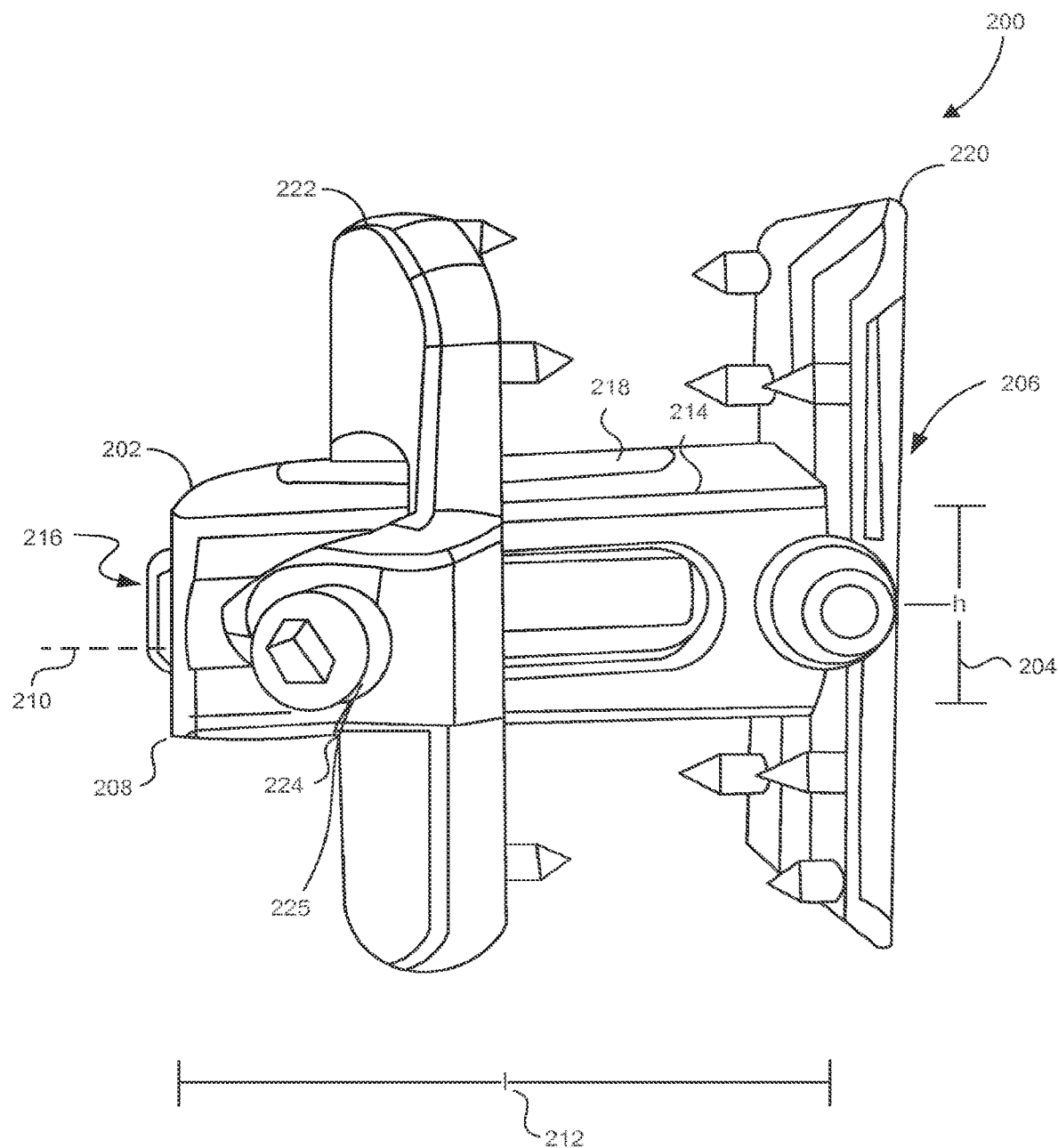
FIG. 10 is a perspective view of an implant that is consistent with the technology of the present application.

FIG. 10 provides a perspective view of an exemplary implant 200. The implant 200 includes a spacer 202 that is sized and shaped to be fitted between adjacent spinous processes, such as processes 20, 21 in FIGS. 1 and 2. The spacer 202 has a height h 204 extending in the cephalic/caudal direction. The height h 204 limits how closely the spinous processes can move together and functions as an extension stop. As will be explained further below, the implant 200 may be further fixed to the spinous processes such that the implant 200 also limits how far the spinous processes can move apart such that the implant 200 is a flexion inhibitor as well, which facilitates fusion as the spinal segments are immobilized with respect to each other. The spacer 202 has a first end 206, a second end 208, and a longitudinal axis 210 defining a length l 212 of the spacer. The length l 212 of the spacer is in the medial/lateral direction. The length l 212 is sufficient to allow the spacer 202 to traverse an interspinous space between adjacent spinous processes, such as processes 20, 21. The spacer 202 is shown having a shape 214, which in this case is cubic, but other shapes are possible including cylindrical, frusto-conical, or even random shapes to accommodate patient anatomy. The spacer 202 forms an internal area 216, which will be explained further below.

The spacer 202 may include opening 218 in the cephalic and caudal surfaces and/or the anterior and posterior surfaces. The opening 218 may be elongated slots as shown, bores, perforations, micro pores, or the like. The openings 218 allow for tissue or boney in-growth to form between the adjacent spinous processes to facilitate fusion. The spacer 202 may be filled with bone growth promoting substances as described above.

Implant 200 includes a first extension 220 and a second extension 222. In the deployed position, both first and second extensions 220, 222 extend outwardly from the longitudinal axis 210 to lie generally alongside the superior and inferior spinous processes. Unlike implant 100 described above, spacer 202, first extension 220, and second extensions 222 may be of a modular construction as will be explained further below. This provides for different sized spacers and extensions to be mixed and matched based on the patient's anatomy or other surgical concerns. While modular, in this exemplary embodiment, the first extension 220 does not traverse over the spacer 202 as does the second extension 222. The first extension 220 when deployed may abut the first end 206 of spacer 202. The second extension 222 is mountable to the spacer 202 at the second end 208 and may be moved toward the first extension 220 until the surgeon is satisfied with the placement of the second extension 222 or the spinous processes inhibit further movement. Once placed, a locking fastener 224 is placed to lock both first and second extension 220, 222 in place on spacer 202.

Figure 11:
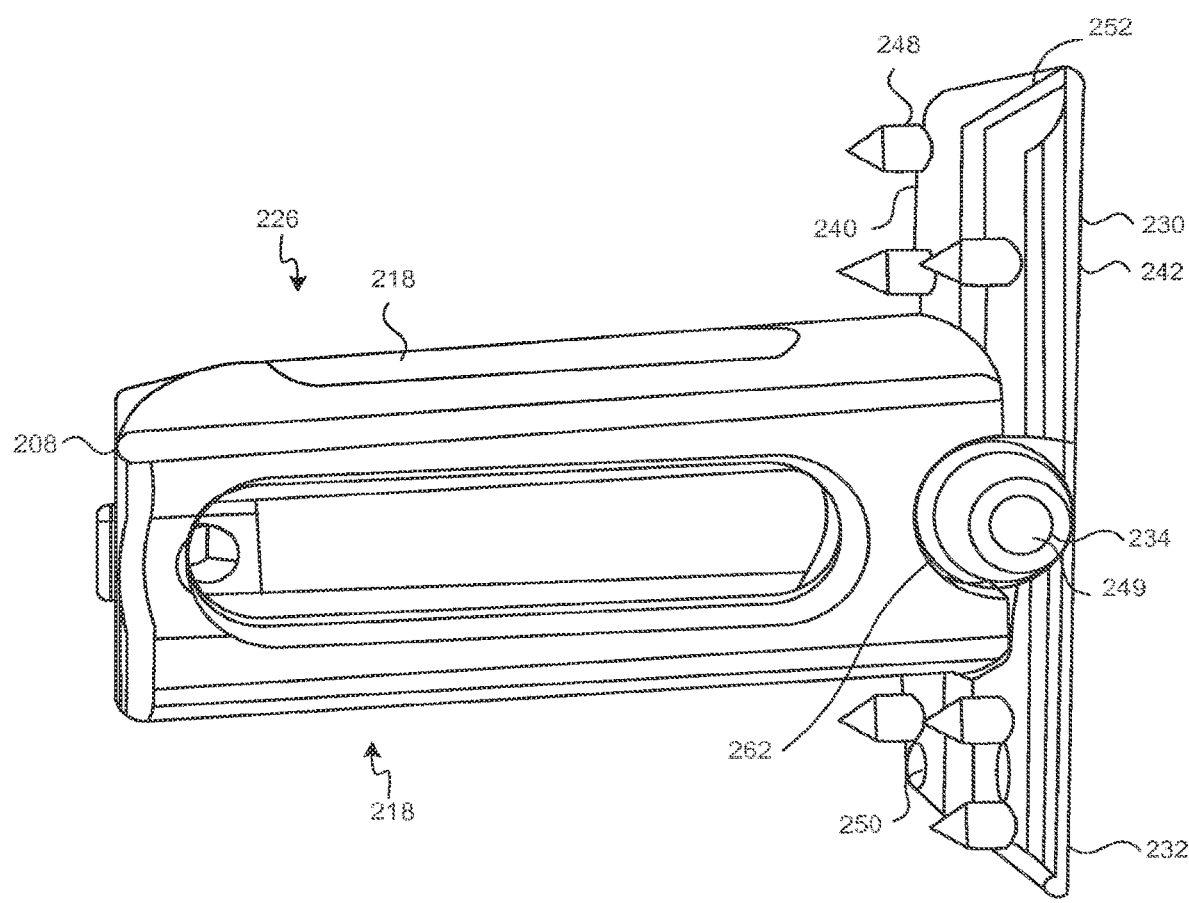
FIG. 11 is a perspective view of a portion of the implant of FIG. 10 in an unfolded configuration.
Figure 12:
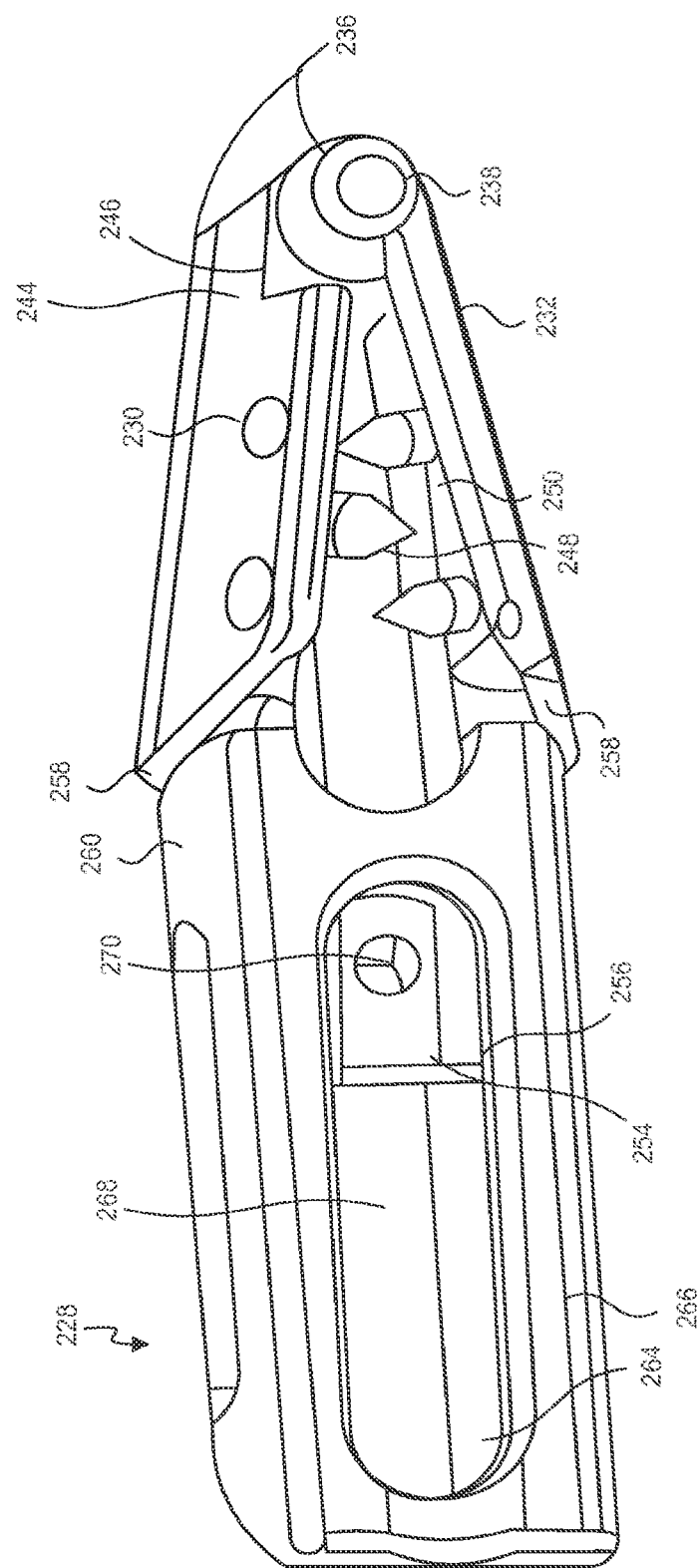
FIG. 12 is a perspective view of a portion of the implant of FIG. 10 in a folded configuration.

Referring now to FIGS. 11 and 12, implant 200 is shown with the spacer 202 and the first extension 220. FIG. 11 shows first extension 220 in the unfolded position 226; whereas. FIG. 12 shows first extension 220 in a partially folded position 228. In certain embodiments, first extension 220 would fold until a superior lobe 230 collapsed into the inferior lobe 232. Alternatively superior lobe 230 and inferior lobe 232 may collapse until engaging the outer surface of spacer 202. The superior lobe 230 is rotationally coupled to inferior lobe 232 by a hinge joint 234. While a number of hinge joints or rotational connections are possible, in this exemplary embodiment, hinge joint 234 is formed by inferior lobe 232 having bosses 236, such as extended flanges or protrusions, with detents or bores 238 on each of an anterior side 240 and a posterior side 242 of the first extension 220. Fitting between the flanges 236 is a tab 244 coupled to the superior lobe 230. The tab 244 has a bore 246 (not specifically shown) that aligns with the detents or bores 238. An axle or pin 249 extends from the detent or bore 238 on the anterior side 240, through the bore 246 to the detent or bore 238 on the posterior side 242. While not specifically shown, the hinge may incorporate a spring, such as, for example, a torsion spring, to facilitate folding or unfolding of the superior and inferior lobes.

The hinge joint 234 also serves as a distracter during insertion. In particular, the rounded or bulbous surface of the hinge joint 234 allows for tissue separation or distraction. The distracted tissue than travels along the outer surface of the superior, inferior lobes 230, 232 facilitating insertion of the implant 200.

The first extension 220 has a plurality of fasteners 248 on both the anterior side 240 and the posterior side 242. The first extension 220 also has a plurality of bores 250 on both the anterior side 240 and the posterior side 242. While the specific arrangement is largely a matter of design choice, strength, and function, each fastener on the anterior side has a corresponding bore on the posterior side and each fastener on the posterior side has a corresponding bore on the anterior side. Thus, when collapsed, the fasteners 248 align with the corresponding bore 250 to allow the superior lobe to fully collapse into the inferior lobe. Of course, the fasteners may be adjustable, removable, or deployable in groups in a manner consistent with the fasteners described above. In certain embodiments, any foldable extensions may forego fasteners to facilitate unfolding. The bores 250 when not occupied by a fastener provide further fenestration of the extensions, which facilitates boney or tissue in-growth through the extensions. The bores 250 may be packed with bone or tissue growth promoting substances similar to the spacer 202.

The first extension 220 also forms a channel 252. The channel 252 is sized to fit a draw 254 that is connected to the hinged joint 234. The draw 254 is sized to fit within the internal area 216 and move between first and second ends 206, 208. The draw 254 may terminate in a flanged surface 256 to inhibit removal of the draw after implantation. In this case, the first end 206 of spacer 202 may be swaged or pinched after the draw if fitted to the internal area 216 to capture the draw. The draw 254 may be connectable to an instrument such as, for example, a hook, via a port 270 or dimple, for example, such that the draw may be moved from the first end 206 towards the second end 208 to cause the superior lobe 230 and the inferior lobe 232 to unfold. The instrument also may be used to maintain first extension 220 and spacer 202 coupled during implantation until locking fastener 224 may be used to lock the implant 200. The posterior side 266 of the spacer 202 may include an enlarged slot 268 or window to facilitate a tool's connection to the port 270.

Each of the superior lobe 230 and inferior lobe 232 terminate at an edge 258. The edges 258 may be chamfered to facilitate movement of the lobes 230, 232 across a pair of bluffs 260 on spacer 202 at the first end 206. The edges may be designed to facilitate scraping tissue to facilitate movement of the lobes 230, 232 into an unfolded position. The bluff 260 also may be chamfered to facilitate movement of the lobes 230, 232 across the bluffs. The first end 206 of spacer 202 may include a detent 262 to accept the hinge joint 234 to allow the lobes 230, 232 to fully extend. By moving the draw 254, the lobes 230, 232 may be deployed in a range of angles depending on patient anatomy. Generally, the lobes 230, 232 will form planar surfaces, but the lobes may be arranged as required including, in some embodiments, past a planar surface such that the lobes start folding back on themselves. FIG. 11 shows lobes 230, 232 forming about a 180° angle, but the lobes 230, 232 may form an angle in the deployed condition from about 170° to about 190°.

The internal area 216 may be defined by a surface 264. The second end 208 may include one or more protrusions or ratchets (not particularly shown) radially extending from surface 264 into the internal area 216. The flanged surface 256 may engage the protrusion to provide a lock, or at least a temporary lock, for the first extension 220 until second extension 222 is placed on spacer 202 and lock fastener 224 locks the implant 200.

Figure 13:
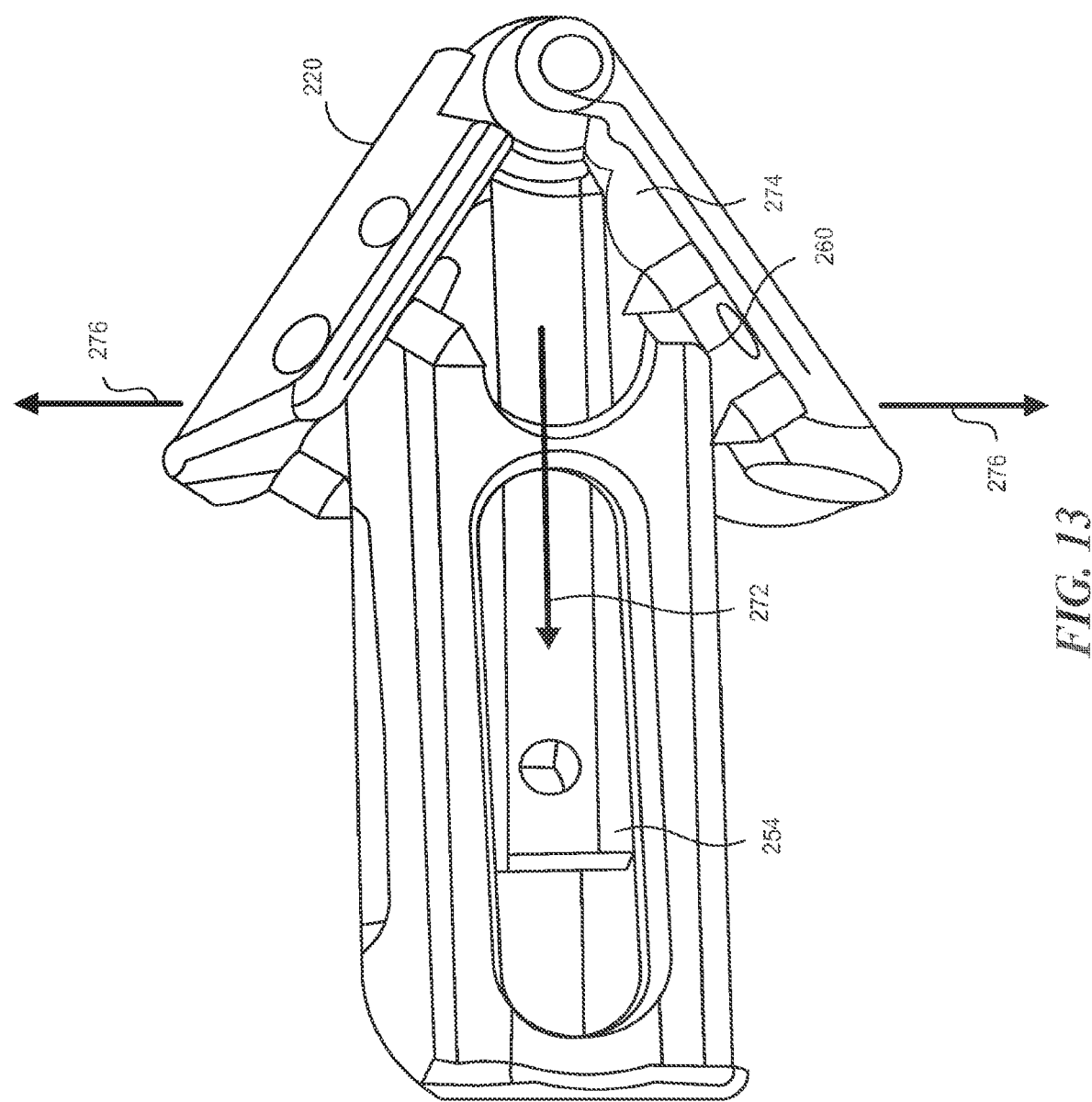
FIG. 13 is a perspective view of a portion of the implant of FIG. 10 in a partially unfolded configuration.

FIG. 13 shows implant 200 with first extension 220 partially deployed. As shown by FIG. 13, moving the draw in the direction shown by arrow 272 causes the inner surfaces 274 of the lobes 230, 232 to move against the bluffs 260. As the inner surfaces 274 move against the bluffs 260, the lobes 230, 232 move in the direction shown by arrows 276 and unfold or open. While not specifically shown, second extension 222 may be constructed similar to first extension 220 to allow for folding and unfolding of the second extension as well. In this case, the draws 254 may meet midline in this case. Alternatively, the draws may be arranged such that one draw moves across the other.

Once implant 200 is implanted such that spacer 202 resides in the interspinous space, and first and second extensions 220, 222 abut the spinous processes, the implant 200 is compressed such that fasteners 248 fix the implant to the spinous processes. In one embodiment, a tool to compress the implant pulls on the draw 254 and pushes on second extension 222 causing the fasteners 248 on the first, second extensions 220, 222 to clamp onto the spinous processes. Subsequent to the clamping, lock fastener 224, such as a set screw, pin, rivet, or the like is removably connected to second extension 222 through a bore 225. The head of the lock fastener is retained in the bore 225 while the shaft of the fastener extends through the bore and the enlarged slot 268 to press, pinch, or clamp the draw 254 on the anterior side of the surface 264 defining internal area 216.

Figure 14:
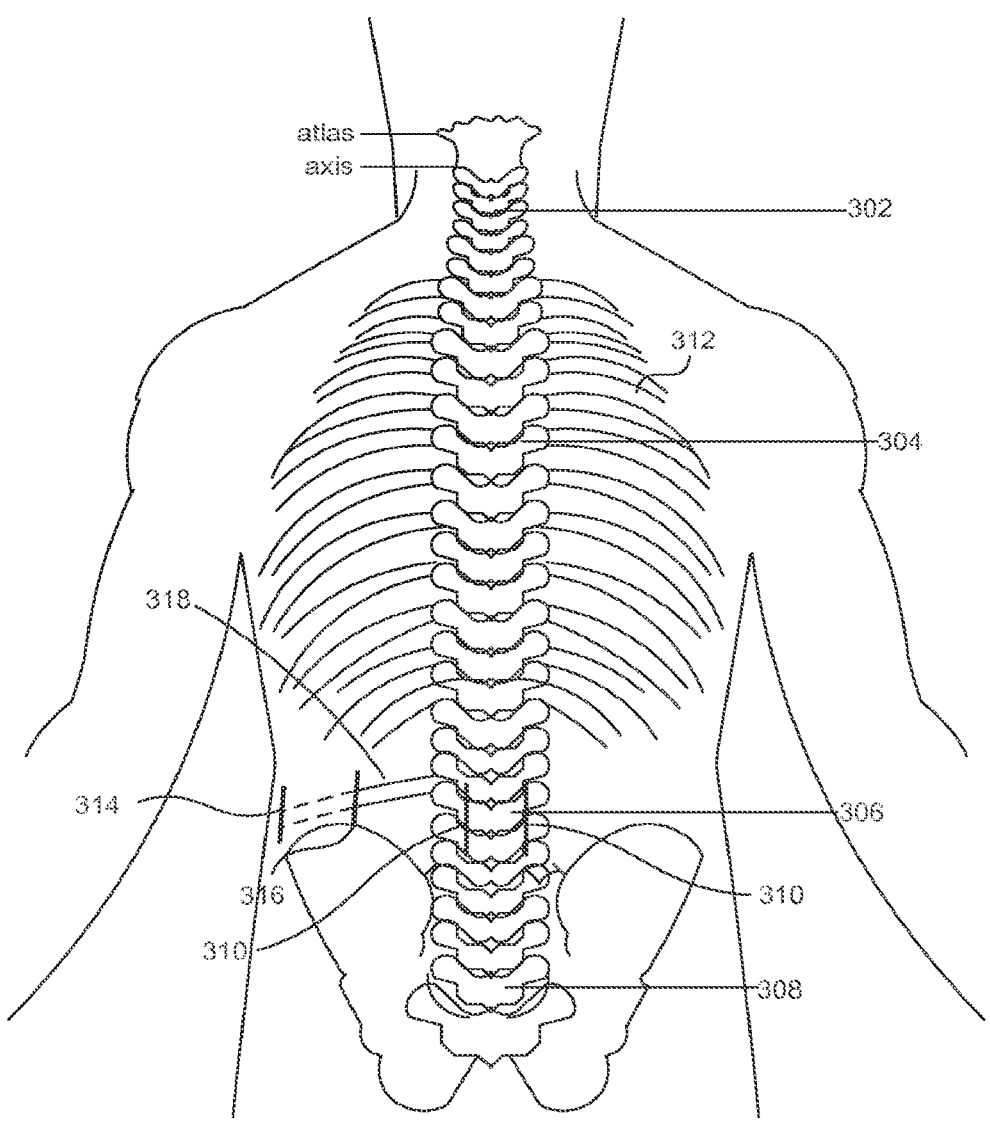
FIG. 14 is a view of surgical access to surgically implant the implant of FIG. 10.

Referring now to FIG. 14, a posterior view of a spine 300 is provided. As can be appreciated, spine 300 may be divided into the cervical vertebrae 302, the thoracic vertebrae 304, the lumbar vertebrae 306, and the sacrum 308. Traditionally, spinous process implants, such as implant 100 above, are surgically deployed by a surgeon making one or two incisions 310 on a patient's posterior region 312. FIG. 14 shows two incisions. For implant 100 above, the spacer 102 and first extension 126 would be implanted in one of the two incisions 310 and placed in the interspinous space with the first extension 126 on one side of the adjacent spinous processes. The second extension would be implanted through the other incision 310 and mated with the spacer 102 on the other side of the adjacent spinous processes. Alternatively, one midline incision 310 may be used instead of the two slightly off midline incisions 310 as shown. The ability of implant 200 to fold provides for an alternative implantation strategy. Instead of a midline incision to provide access to the surgical site, which generally involves significant tissue trauma, a lateral or paramedian incision may be made to provide a less traumatic approach to the surgical site. In these approaches, a single incision (either incision 314 or incision 316) may be made lateral of the spine. A surgical corridor 318 may be established from the incision to the interspinous space to allow for implantation of the implant 200. The surgical corridor 318 may be formed by a catheter, a lumen, a tube, or the like as is generally known in the industry. In a particular embodiment, implant 200 is used in conjunction with a lateral approach to the spine for an interbody procedure. In a particular embodiment, a patient in need of a fusion at one or more spinal levels undergoes a lateral surgical procedure in which a surgical corridor is made to the desired disc space from the patient's side. For some lumbar procedures, this may involve traversing the psoas muscle. Once the interbody implant has been placed, implant 200 can be positioned between the spinous processes at the same level. This may occur, for example, by at least partially using the same surgical corridor created for the interbody insertion. Alternatively, a separate, laterally-oriented corridor can be created to the interspinous space. In either case, the procedures may be performed with minimal or no patient repositioning being required.

Figure 15:
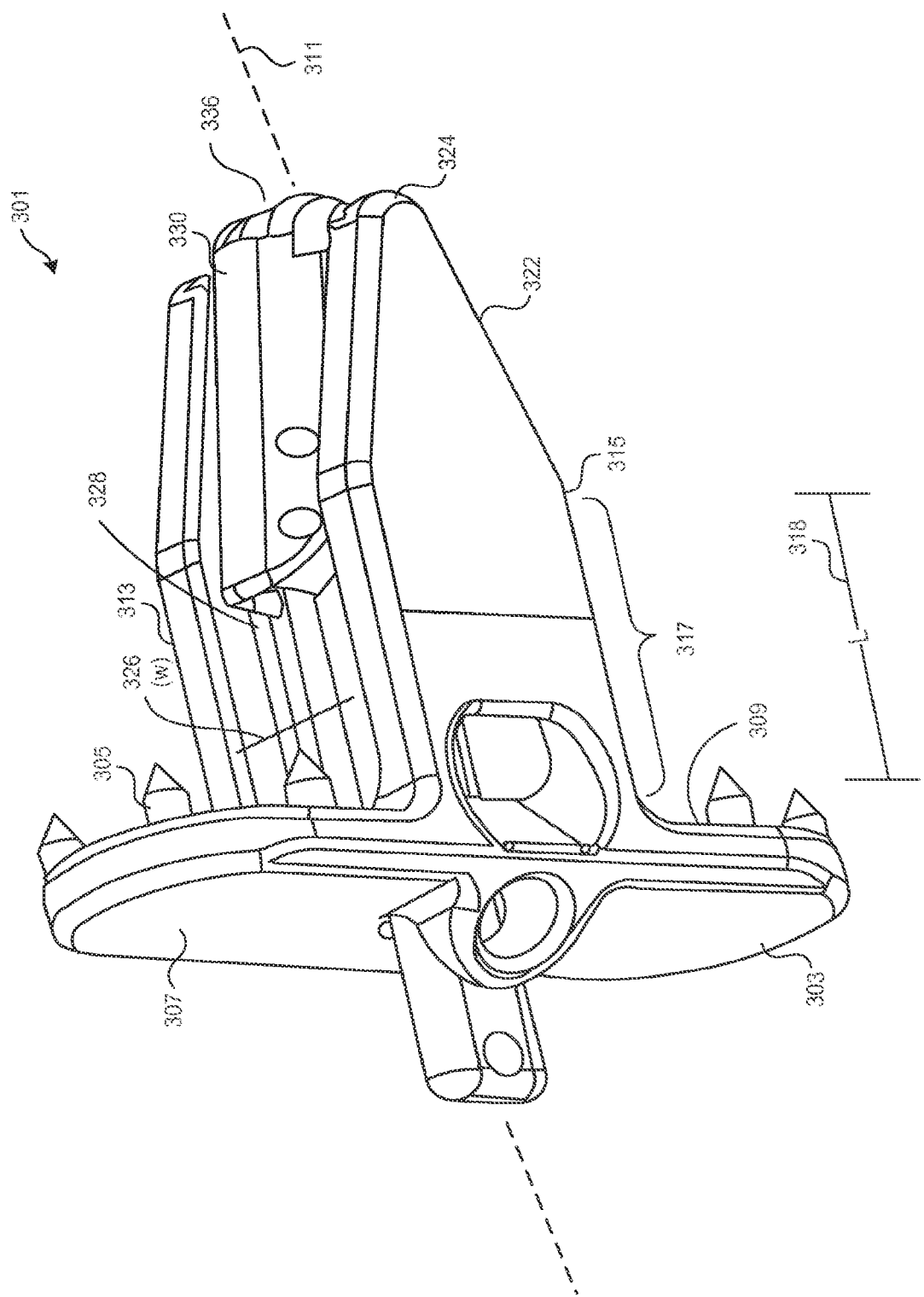
FIG. 15 is a perspective view of an implant that is consistent with the technology of the present application in a folded configuration.

A perspective view of an implant 301 exemplary of the technology of the present application is shown in FIG. 15. The implant 301 has a fixed extension 303 with fasteners 305 coupled to the fixed extension 303. The fixed extension 303 is sized to abut a first side of adjacent spinous processes. While described abutting a first side of the adjacent spinous process, bone or tissue growth promoting substances may be placed between the fixed extension 303 and the adjacent spinous process to facilitate fusion, for example. The growth promoting substance may be a bone sheet, an allograph or autograph washer, a plasma coating, demineralized bone matrix (DBM), bone morphogenic proteins (BMP), or the like. Fasteners 305 are consistent with the fasteners 132, 134, and 136 described above with respect to implant 100. The fixed extension 303 is shown with a superior lobe 307 and an inferior lobe 309 that are symmetrical about a midline axis 311 of implant 301. The superior and the inferior lobes 307, 309 may be asymmetrical to account for patient anatomy or the like. Also, the superior and the inferior lobes 307, 309 may be offset in an anterior or posterior direction to facilitate interleaving of implants 301, such as, for example, the Z-shape shown in FIG. 9. While shown as a solid plate like device, fixed extension 303 may include one or more openings or fenestrations to allow for bone or tissue growth through the fixed extension 303, which would facilitate fusion.

Integral with the fixed extension 303 are a pair of cantilevered arms 313, 315. In this exemplary embodiment, cantilevered arm 313 is anterior to cantilevered arm 315. While shown as a pair of cantilevered arms, a single cantilevered arm is possible. If a single cantilevered arm is used, the lock fastener, as described below, may be arranged to pinch the draw to the single cantilevered arm. The cantilevered arms 313, 315 have a main body portion 317 extending from the fixed extension 303. The main body portion is of a sufficient length L 318 extending parallel to the midline axis 311 to traverse an interspinous process gap. The main body portion also includes a height H 320 extending in the cephalic/caudal direction. The height H 320 limits how closely the spinous process can move together and functions as an extension stop. The cantilevered arms 313, 315 further have a tapered portion 322 that extends from the main body portion at a location distal from the fixed extension 303. The tapered portion 322 has a decreasing height from the height H 320 to a tip 324 of the tapered portion that forms a bulbous nose. The tapered portion 322 facilitates movement of tissue from the surgical space during implantation and may function to facilitate distraction of the adjacent spinous processes.

The cantilevered arms 313, 315 are spaced apart a width w 326 that extends in an anterior/posterior direction. The space between the cantilevered arms 313, 315 forms an area 328 that is generally open to allow for a folding wing 330, to be explained further below, to fold into and out of the area 328. The area 328 may have portions generally proximate to the fixed extension 303 that have a superior or inferior surface (not specifically shown). Adding a surface spanning the area 328 may facilitate adding bone or tissue growth promoting substances.

Figure 16:
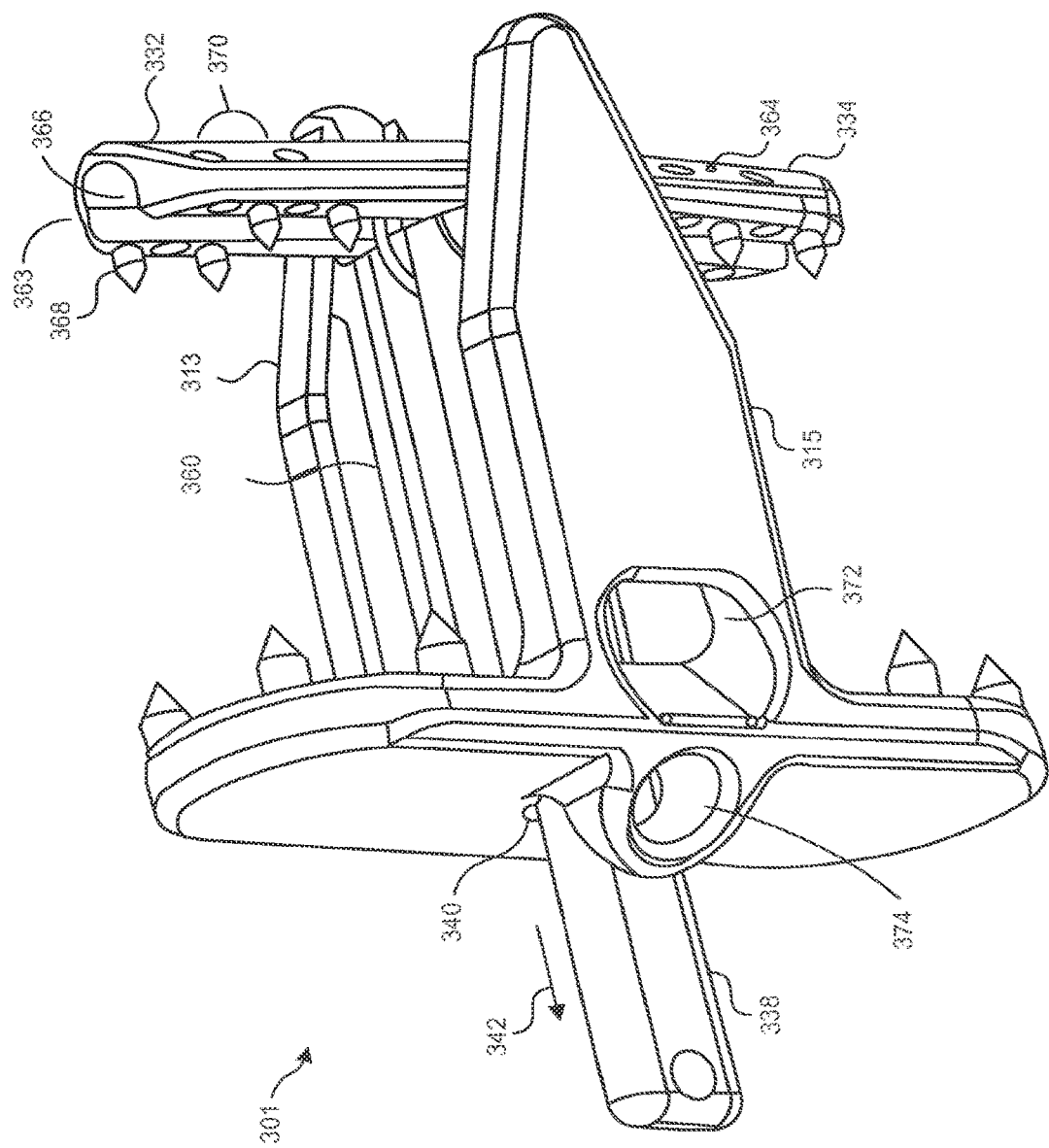
FIG. 16 is a perspective view of the implant of FIG. 15 in an unfolded configuration.

The implant 301 also comprises the folding extension 330 contained in the tapered portion 322 of the cantilevered arms 313, 315 as shown in FIG. 15. The folding extension 330 includes a superior lobe 332 and an inferior lobe 334 that can be collapsed onto each other as shown in FIG. 15 or expanded into an unfolded position as shown in FIG. 16. The superior lobe 332 and the inferior lobe 334 are pivotally or rotationally connected by a hinge joint 336. A draw 338 is connected to hinge joint 336 and extends in the area 328 between the cantilevered arms 313, 315 through an aperture 340 in fixed extension 303. Moving the draw 338 in a direction as shown by arrow 342 causes the superior and inferior lobes 332, 334 to expand or unfold.

Figure 17:
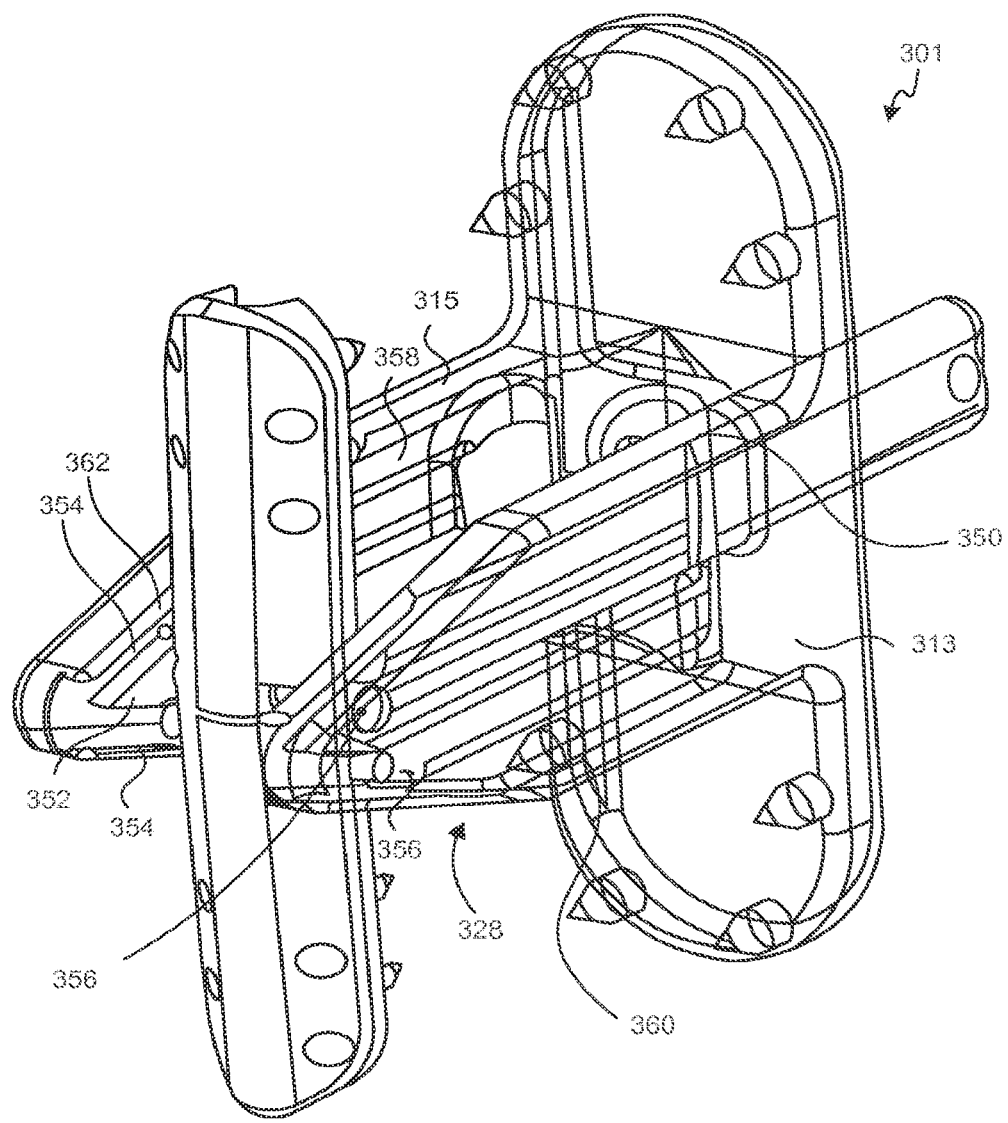
FIG. 17 is a perspective view of the implant of FIG. 15 with a portion of the implant transparent.

FIG. 17 is a partial line diagram facilitating the description of the area 328. The cantilevered arms 313, 315 have inside surfaces 350, 352 opposing each other. The inside surface 350, 352 contain grooves 354, 356, 358, and 360. Correspondingly, superior lobe 332 and inferior lobe 334 have tongues, protrusions, or tabs 362 that sliding mate with grooves 354, 356, 358, and 360. In the folded position, as shown in FIG. 15, the tabs 362 are proximate the hinged joint 336. Grooves 354 and 356 form ramps such that moving draw 338 in the direction of arrow 342 causes the protrusions 362 to move along the ramps 354 and 356 forcing the protrusions 362 to move away from each other, which causes superior and inferior lobes 332, 334 to unfold, expand, separate, or deploy as shown. Grooves 354 and 356 communicate with essentially horizontal grooves 358 and 360. Once opened, the protrusions 362 move from ramp grooves 354, 356 to horizontal grooves 358, 360 such that further movement of the draw 338 in the direction of the arrow 342 causes compression of the fixed extension 303 and the folding extension 330 to clamp or pinch the spinous processes.

With reference back to FIG. 16, the folding extension 330 is shown in the expanded position. The folding extension 330 includes an anterior side 363 and a posterior side 364 separated by a channel 366. The channel 366 is sized to fit the draw 338 when the folding extension 330 is folded as shown in FIG. 15. The anterior and posterior sides 363, 364 include a plurality of fasteners 368 and a plurality of bores 370. Each fastener on the anterior side has a corresponding bore on the posterior side, and each fastener on the posterior side has a corresponding bore on the anterior side. The fasteners 368 align with and fit into the bores 370 when the folding extension is folded to allow for a more compact implant during implantation. When unfolded, the bores 370 provide additional avenues for bone or tissue growth to facilitate fusion. Bone or tissue growth also is facilitated by area 328 being generally open to allow for the superior and inferior lobes 332, 334 to unfold. To further facilitate bone or tissue growth, one or more windows 372 may be provided in one or more of the cantilevered arms 313, 315. Bone or tissue growth promoting substances may be placed in window(s) 372. Care should be exercised to ensure the window does not interfere with locking the extension.

Once the folding extension 330 is unfolded, and both the fixed extension 303 and folding extension 330 are clamped such that fasteners 305 and 368 engage the spinous processes, the implant is locked such that the folding extension 330 does not move with respect to the fixed extension 303. To accomplish this, a locking bore 374 is provided to receive a locking fastener (not specifically shown). The locking fastener is connected to the locking bore 374 and driven such that the shaft of the locking fastener clamps, or pinches, the draw 338 between the shaft of the locking fastener and one of the inside surfaces 350 or 352. As shown, the locking bore is located in the fixed extension 303, which facilitates access in a lateral or paramedian access procedure, but the locking bore 374 may be positioned at other locations, such as, for example, in the posterior cantilevered arm 315.

Figure 19:
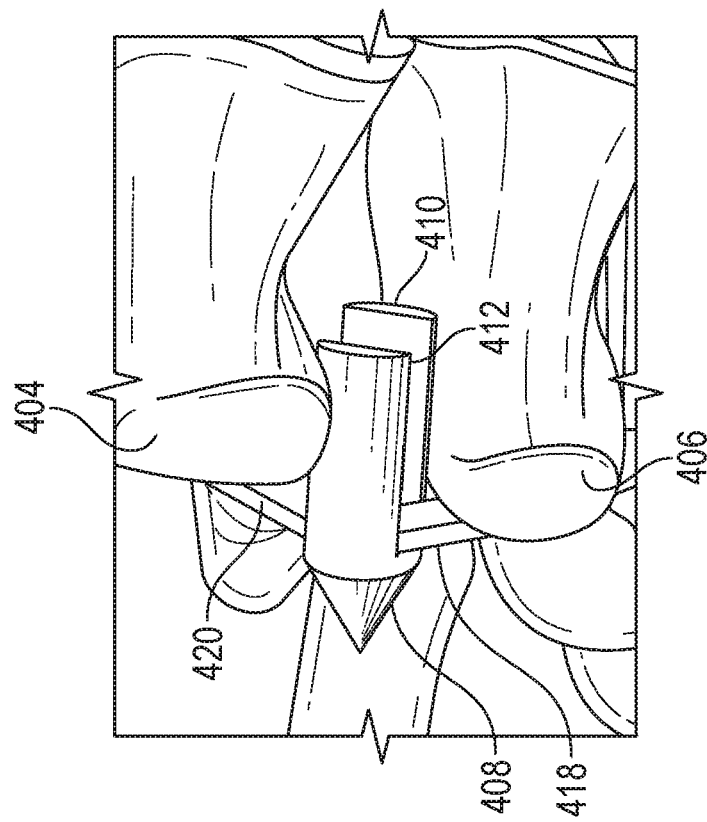
FIGS. 18-21 provide a perspective view of a method of implanting an implant consistent with the technology of the present application.
Figure 18:
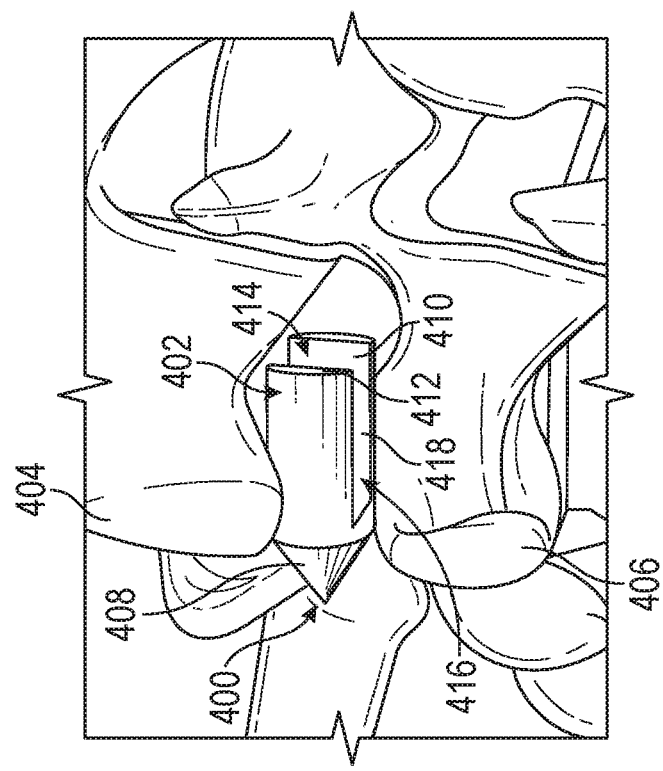
Figure 21:
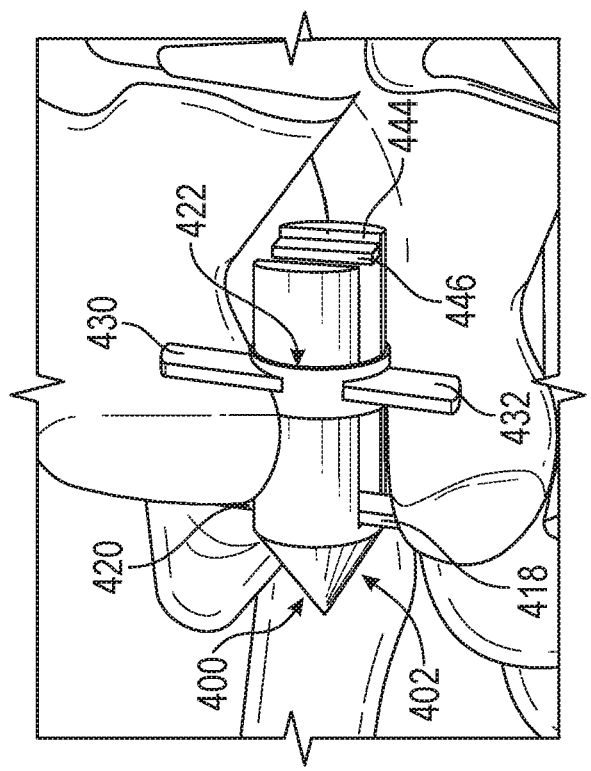
Figure 20:
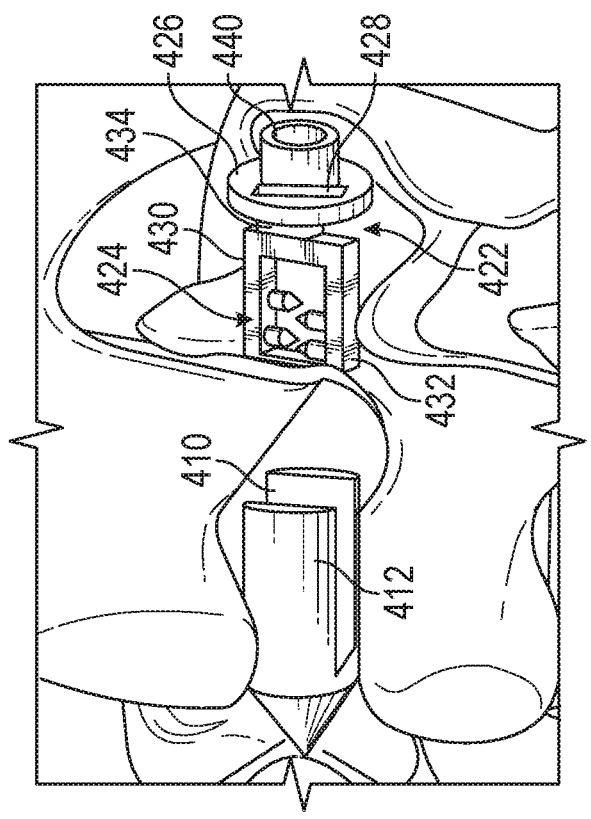

FIGS. 18 to 21 demonstrate a lateral implantation of a modular implant 400. Implant 400 includes a combination of the foldable extensions explained above with respect to implant 200 and 300, which operations will not be re-explained herein. As shown in FIG. 18, a first portion 402 of implant 400 is inserted laterally between adjacent spinous processes 404, 406. The first portion 402 includes a tapered or bulbous lead 408 to facilitate movement of tissue and inserting the implant between the processes 404, 406. Extending from the bulbous lead 408 are a pair of cantilevered arms 410, 412. The cantilevered arms 410, 412 form an area 414 in which a first folding extension 416 resides, of which the inferior lobe 418 is shown in FIG. 18. Once the superior and inferior lobes 420, 418 are past the processes 404, 406, the first folding extension 416 is opened, similar to using the draws explained above with respect to extension 330, for example, as shown in FIG. 19. Once the first portion 402 and the first folding extension 416 are placed, as shown in FIG. 20, the second portion 422 of implant 400 with second folding extension 424 is inserted. The second portion 422 includes a base 426 shaped to cooperatively engage the cantilevered arms 410, 412 and move along the cantilevered arms 410, 412. In this particular exemplary embodiment, the base 426 is a disc shape with a pair of slots 428 shaped to allow the cantilevered arms 410, 412 to be received in the slots 428. The second folding extension 424 has superior and inferior lobes 430, 432 that are coupled to the base 426 through a hinge joint 434 or the like. Similarly to first extension 220, the second folding extension 424 may have leading edges that move against bluff surfaces to cause the superior and inferior lobes to expand. In certain embodiments, the second portion 422 may include a driver 440 coupled to a gear or the like such that rotation of the driver 440 causes the superior and inferior lobes 430, 432 to open. The base 426 is moved along the cantilevered arms 410, 412 until a desired position is reached. The device may be locked by a set screw or lock fastener as described above. Alternatively, the opposed inner surfaces 444 of the cantilevered arms may have ribs 446 that form a ratchet lock with protrusions 442 on base 426. The ratchet lock maintains the implant 400 in the desired orientation with respect to the spinous processes as shown in FIG. 21.

Although examples of a spinous process implant and associated instruments and techniques have been described and illustrated in detail, it is to be understood that the same is intended by way of illustration and example only and is not to be taken by way of limitation. Accordingly, variations in and modifications to the spinous process implant, instruments, and technique will be apparent to those of ordinary skill in the art, and the following claims are intended to cover all such modifications and equivalents.

We claim:

1. An apparatus adapted for placement in an interspinous space between adjacent spinous processes comprising:
    a first extension comprising a superior lobe and an inferior lobe, the first extension including an aperture, the superior lobe adapted to reside proximate a superior spinous process and the inferior lobe adapted to reside proximate an inferior spinous process;
    at least one arm having a first surface extending from the first extension, the at least one arm comprising a main body portion coupled to the first extension and a tapered portion that extends from the main body portion distal from the first extension, the main body portion having a length sufficient to transverse a space between the superior and inferior spinous process and the tapered portion terminating in a tip, the first surface comprising at least one groove;
    a foldable extension having a superior lobe pivotally connected to an inferior lobe to allow the foldable extension to move from a folded position to an unfolded position, at least one of the superior and inferior lobe comprising at least one protrusion movably engaged in the at least one groove,
    a draw having a first end and a second end opposite the first end, the draw being connected to the foldable extension at the first end, the draw extending through the aperture of the first extension, wherein the draw is movable through the aperture to cause the at least one protrusion of the at least one of the superior lobe and the inferior lobe of the foldable extension to move in the at least one groove such that the superior lobe and the inferior lobe unfold, and at least a second arm having a second surface opposing the first surface to define a space, the second arm extending from the first extension and comprising a main body portion coupled to the first extension and a tapered portion that extends from the main body portion distal from the first extension, the main body portion having a length sufficient to transverse a space between the superior and inferior spinous process and the tapered portion terminating in a tip, the second surface comprising at least one groove;

wherein the at least one groove in each of the first surface and the second surface comprises a first groove in the tapered portion forming a generally V shaped ramp and a second groove in the main body portion extending generally horizontal.

2. The apparatus of claim 1, wherein the first extension is non-foldable.

3. The apparatus of claim 1, wherein the first extension further comprises a lock bore and a lock fastener, the lock fastener engagable with the lock bore to lock the foldable extension in place with respect to the first extension.

4. The apparatus of claim 3, wherein the lock fastener clamps the draw between a shaft of the lock fastener and a surface of the aperture.

5. An interspinous implant comprising:
a fixed extension comprising:
  a fixed superior lobe;
  a fixed inferior lobe;
  a first cantilevered arm extending from the fixed extension along a midline axis; and
  a second cantilevered arm extending from the fixed extension along the midline axis spaced from the first cantilevered arm such that an area is formed between the first and second cantilevered arms extending from the fixed extension to free ends of the first and second cantilevered arms;
a folding extension comprising:
  a folding superior lobe;
  a folding inferior lobe; and
  a hinge joint coupling the folding superior lobe and the folding inferior lobe; and
a sliding tab and groove coupling between the folding extension and the fixed extension, the sliding tab and groove coupling comprising:
  a first pair of ramped grooves on the first cantilevered arm:
  a second pair of ramped grooves on the second cantilevered arm:
  a first pair of tabs extending from the folding superior lobe; and
  a second pair of tabs extending from the folding inferior lobe:
  wherein the first pair of tabs and the second pair of tabs engage with the first pair of grooves and the second pair of grooves to form a sliding connection; and
  ramped wherein the first pair of ramped grooves and the second pair of ramped grooves extend away from the fixed superior lobe and the fixed inferior lobe in a direction parallel to the midline axis and bend inward toward the midline axis distal to the fixed superior lobe and the fixed inferior lobe.

6. The interspinous implant of claim 5, wherein:
the first pair of ramped grooves includes a first superior groove and a first inferior groove; and
the second pair of ramped grooves includes a second superior groove and a second inferior groove.

7. The interspinous implant of claim 6, wherein:
the first pair of tabs includes:
  a first tab extending from a first side of the folding superior lobe for riding in the first superior groove; and
  a second tab extending from a second side of the folding superior lobe for riding in the second superior groove; and
the second pair of tabs includes:
  a third tab extending from a first side of the folding inferior lobe for riding in the first inferior groove; and
  a fourth tab extending from a second side of the folding inferior lobe for riding in the second inferior groove.

8. The interspinous implant of claim 5, further comprising a draw extending from a first end at the folding extension proximate the hinge joint toward a second end extending through an opening in the fixed extension.

9. The interspinous implant of claim 8, wherein the draw is configured to be:
withdrawn from the opening to rotate the folding superior lobe and the folding inferior lobe away from each other at the hinge joint; and
pushed into the opening to rotate the folding superior lobe and the folding inferior lobe toward each other at the hinge joint.

10. The interspinous implant of claim 8, wherein the folding superior lobe and the folding inferior lobe include channels sized to receive the draw.

11. The interspinous implant of claim 10, wherein the channels extend to the free ends of the first and second cantilevered arms such that the folding superior lobe and the folding inferior lobe can engage the draw between the first and second cantilevered arms.

12. The interspinous implant of claim 5, further comprising first and second windows formed in the first and second cantilevered arms, respectively, to provide access to the area.

13. An interspinous implant comprising:
a fixed extension extending from a fixed superior lobe to a fixed inferior lobe;
a pair of opposing arms extending transversely from the fixed extension along a midline axis toward cantilevered ends, each arm of the pair of opposing arms including at least one groove; and
a folding extension comprising a folding superior lobe and a folding inferior lobe joined at a hinge joint, wherein one of the folding superior lobe and the folding inferior lobe includes a pair of tabs to engage the at least one groove in each arm;
wherein the at least one groove in each arm are shaped such that the superior folding lobe and the inferior folding lobe extend in a superior-inferior direction when the hinge joint is proximate the fixed extension and collapse into an at least partially medial-lateral orientation when the hinge joint is pushed proximate the cantilevered ends;
wherein the at least one groove in each arm extend parallel to the midline axis proximate the fixed extension and ramp inward toward the midline proximate the cantilevered ends.

14. The interspinous implant of claim 13, further comprising a draw comprising:
a first end attached to the folding extension proximate the hinge; and
a second end protruding through the fixed extension.

15. The interspinous implant of claim 14, wherein the folding superior lobe and the folding inferior lobe each include a channel that receive the draw in the at least partially medial-lateral orientation such that the folding superior lobe and the folding inferior lobe are capable of being recessed in between the pair of opposing arms.

* * * * *

UNITED STATES PATENT AND TRADEMARK OFFICE
CERTIFICATE OF CORRECTION

PATENT NO. : 10,561,447 B2
APPLICATION NO. : 15/672786
DATED : February 18, 2020
INVENTOR(S) : Taber et al.

Page 1 of 1

It is certified that error appears in the above-identified patent and that said Letters Patent is hereby corrected as shown below:

In the Claims

In Column 15, Line 46, in Claim 5, delete "arm:" and insert --arm;-- therefor

In Column 15, Line 48, in Claim 5, delete "arm:" and insert --arm;-- therefor

In Column 15, Line 52, in Claim 5, delete "lobe:" and insert --lobe;-- therefor

In Column 15, Line 57, in Claim 5, before "wherein", delete "ramped"

Signed and Sealed this
Third Day of November, 2020

Andrei Iancu
*Director of the United States Patent and Trademark Office*